(12) United States Patent
Ahn et al.

(10) Patent No.: US 10,705,064 B2
(45) Date of Patent: Jul. 7, 2020

(54) MICRO SENSOR PACKAGE

(71) Applicant: POINT ENGINEERING CO., LTD., Asan (KR)

(72) Inventors: Bum Mo Ahn, Suwon (KR); Seung Ho Park, Hwaseong (KR); Tae Hwan Song, Cheonan (KR)

(73) Assignee: POINT ENGINEERING CO., LTD., Asan (KR)

( * ) Notice: Subject to any disclaimer, the term of this patent is extended or adjusted under 35 U.S.C. 154(b) by 298 days.

(21) Appl. No.: 15/702,666

(22) Filed: Sep. 12, 2017

(65) Prior Publication Data

US 2018/0074033 A1    Mar. 15, 2018

(30) Foreign Application Priority Data

Sep. 13, 2016    (KR) .................. 10-2016-0118019

(51) Int. Cl.
  *H01G 5/012*    (2006.01)
  *G01N 33/00*    (2006.01)
  *G01N 27/04*    (2006.01)

(52) U.S. Cl.
  CPC ......... *G01N 33/0027* (2013.01); *G01N 27/04* (2013.01)

(58) Field of Classification Search
  None
  See application file for complete search history.

(56) References Cited

U.S. PATENT DOCUMENTS

| 2006/0049059 | A1* | 3/2006 | Chao ............... | B82Y 30/00 205/323 |
| 2010/0134948 | A1* | 6/2010 | Park ............... | G01N 27/223 361/286 |
| 2015/0027224 | A1* | 1/2015 | Schiffer ............ | G01L 19/147 73/431 |
| 2016/0195488 | A1* | 7/2016 | Ensor ............... | G01N 33/0047 422/69 |

FOREIGN PATENT DOCUMENTS

| CN | 105445420 A | 3/2016 |
| JP | 2008-107105 A | 5/2008 |
| JP | 2012-078089 A | 4/2012 |
| JP | 2012-098233 A | 5/2012 |
| JP | 2012-098234 A | 5/2012 |
| KR | 10-0652571 B1 | 12/2006 |
| KR | 10-2016-0035820 A | 4/2016 |
| KR | 10-2016-0087546 A | 7/2016 |

* cited by examiner

*Primary Examiner* — Ali Naraghi

(57) ABSTRACT

Disclosed is a microsensor package. Particularly, disclosed is a microsensor package configured such that a substrate with a sensor electrode is formed with a plurality of pores penetrating vertically therethrough, the lower surface of the substrate is formed with a bonding portion, and the pores under the sensor electrode pad are provided therein with respective connecting portions electrically connecting the sensor electrode pad and the bonding portion, whereby it is possible to provide a light, slim, and compact microsensor package, and it is possible to mount the microsensor package to a printed circuit board (PCB) without wire bonding.

11 Claims, 6 Drawing Sheets

MICRO SENSOR PACKAGE

CROSS REFERENCE TO RELATED APPLICATION

The present application claims priority to Korean Patent Application No. 10-2016-0118019, filed Sep. 13, 2016, the entire contents of which is incorporated herein for all purposes by this reference.

BACKGROUND OF THE INVENTION

Field of the Invention

The present invention relates generally to a microsensor package. More particularly, the present invention relates to a microsensor package configured such that a substrate with a sensor electrode is formed with a plurality of pores penetrating vertically therethrough, the lower surface of the substrate is formed with a bonding portion, and the pores under the sensor electrode pad are provided therein with connecting portions electrically connecting the sensor electrode pad and the bonding portion.

Description of the Related Art

A conventional micro package for a gas sensor capable of sensing the amount of gas is shown in FIG. 1, which will be briefly described as follows.

A chip mounting portion 2 is formed at a predetermined depth in a central part of a body part 1 that is in the form of a quadrangular plate made of an insulating material, and a sensor chip 4 is attached to the bottom surface of the chip mounting portion 2 by using an epoxy 3.

A plurality of circuit lines 5 are formed inside the body part 1, and a stepped portion 6 having a predetermined height is formed on the inner side edge of the chip mounting portion 2 along the inner circumferential surface thereof.

The stepped portion 6 is formed with an inner terminal 5a extending from a first end of the circuit line 5, and the lower edge of the body 1 is formed with an outer terminal 5b extending from a second end of the circuit line.

The sensor chip 4 is formed with a sensing film 16 at the center of the upper surface thereof to sense gas, and is formed with a plurality of sensor-side terminals 11 at the edge thereof to transmit the resistance change sensed by the sensing film 16 to the outside, such that the sensor-side terminals 11 and the inner terminal 5a of the circuit line 5 are electrically connected to each other by a silver paste 12.

The cap 13 is attached to the upper portion of the body part 1 using an adhesive 14 to cover the chip mounting portion 2, and a plurality of gas holes 15 are formed in the cap 13 to allow the gas to flow into the chip mounting portion 2.

The micro package for a gas sensor configured as described above detects the amount of gas as follows. When the gas flows into the chip mounting portion 2 through the gas holes 15 of the cap 13, a resistance value of the sensing film 16 formed on the upper surface of the sensor chip 4 is changed by the introduced gas, and the resistance value is transmitted to a control unit (not shown) through the circuit line 5, thereby detecting the amount of gas.

However, the conventional micro package for a gas sensor is problematic in that the height of the silver paste that electrically connects the terminals increases the overall height of the package, which limits the production of a light, slim, and compact micro package that can be mounted to a small electronic device.

The conventional micro package is further problematic in that since it is necessary to perform a connection operation for electrically connecting the terminals to each other, there is a limit in reducing the number of manufacturing steps, whereby there is a limit in reducing manufacturing cost.

To solve this problem, Korean Patent. No. 652571 discloses a micro package configured such that a body part is formed with a chip mounting portion with a gas hole communicating with the chip mounting portion, and a circuit line is formed inside the body part, but it is problematic in that since an inner terminal connected to the circuit line at a right angle is required to be formed inside the body part, it is difficult to manufacture.

The foregoing is intended merely to aid in the understanding of the background of the present invention, and is not intended to mean that the present invention falls within the purview of the related art that is already known to those skilled in the art.

DOCUMENTS OF RELATED ART (Patent Document 1) Korean Patent No. 652571;
(Patent Document 2) Japanese Patent No. 5403695;
(Patent Document 3) Japanese Patent No. 5595230; and
(Patent Document 4) Japanese Patent No. 5483443.

SUMMARY OF THE INVENTION

Accordingly, the present invention has been made keeping in mind the above problems occurring in the related art, and an object of the present invention is to provide a light, slim, and compact microsensor package capable of being mounted to a printed circuit board (PCB) without wire bonding.

In order to accomplish the above object, the present invention provides a microsensor package including: a sensing chip, wherein the sensing chip includes a substrate, and a sensor electrode provided on the substrate, the sensor electrode includes a sensor wire, and a sensor electrode pad connected to the sensor wire, the substrate is provided with a plurality of pores formed in vertical directions, the substrate is provided with a bonding portion on a lower surface thereof, the pores under the sensor electrode pad are formed through the substrate in the vertical directions, and the pores under the sensor electrode pad are provided therein with respective connecting portions electrically connecting the sensor electrode pad and the bonding portion to each other.

The sensing chip may be provided with a sensor cap at an upper portion thereof, the sensor cap may have a cavity formed therethrough in a vertical direction, and the sensor wire may be disposed in the lower portion of the cavity.

The microsensor package may further include an anodized aluminum oxide (AAO) filter covering an upper portion of the cavity.

The AAO filter may be coated with a hydrophobic material.

The sensor cap may be made of a material selected from the group consisting of ceramics, plastics, polymers, and aluminum oxides.

The sensor cap may be made of a material with a shrinkage coefficient or an expansion coefficient equal or similar to a shrinkage coefficient or an expansion coefficient of the substrate.

The substrate may be made of an AAO material, and the sensor cap may be made of a ceramic material.

The sensor electrode may be provided in plural on the substrate, and the substrate may be provided on an upper or lower surface thereof with a first cut groove disposed between two neighboring the sensor electrodes.

The sensor electrode may be provided in plural on the substrate, and the sensor cap may be provided on an upper surface thereof with a second cut groove disposed between two neighboring the sensor electrodes.

The second cut groove may have a width gradually reduced in a direction toward the sensing chip.

The sensor cap may have a vertical thickness greater than a vertical thickness of the substrate.

According to the microsensor package of the present invention as described above, effects as follows may be obtained.

Since it is configured such that a substrate with a sensor electrode is formed with a plurality of pores penetrating vertically therethrough, the lower surface of the substrate is formed with a bonding portion, and the pores under the sensor electrode pad are provided therein with connecting portions electrically connecting the sensor electrode pad and the bonding portion, it is possible to provide a light, slim, and compact microsensor package, and it is possible to mount the microsensor package to a printed circuit board (PCB) without wire bonding.

Since it is configured such that the sensing chip is provided with a sensor cap at an upper portion thereof, the sensor cap is formed with a cavity penetrating vertically, and the sensor wire is disposed inside the cavity, it is possible to effectively protect the sensing chip.

Since it further includes an AAO filter covering the cavity, it is possible to effectively prevent foreign matter from being introduced into a gas sensing portion.

Since the AAO filter is coated with a hydrophobic material, it is possible to prevent moisture penetration into the gas sensing portion.

Since the sensor cap is made of a plastic or a polymer material, it has high durability and excellent manufacturability.

Since the sensor cap is made of a material with a shrinkage coefficient or an expansion coefficient equal or similar to that of the substrate, the manufacture thereof is further facilitated, and it is possible to prevent the sensor cap and the substrate from being separated even if they contract or expand.

Since the substrate is made of an anodized aluminum oxide (AAO) material and the sensor cap is made of a ceramic material, it is possible to prevent the heat of the heater electrode formed on the sensing chip from being transmitted to a portion other than the sensing material, mass production is facilitated, and it is possible to prevent the sensor cap and the substrate from being separated even if they contract or expand.

Since it is configured such that the substrate is formed with a plurality of sensor electrodes, and the substrate is provided on the upper or lower surface thereof with a first cut groove disposed between two neighboring the sensor electrodes or the sensor cap is provided on an upper surface thereof with a second cut groove 2200 disposed between two neighboring the sensor electrodes, it is possible to separate the unit package by a simple breaking process, whereby the manufacturing process is simplified because there is no need to cut using a blade.

Since the second cut groove is tapered such that the width thereof is gradually reduced toward the sensing chip, it is possible to separate the unit package more effectively.

Since the sensor cap has a vertical thickness greater than that of the substrate, the substrate of the sensing chip can be separated smoothly when the sensor cap with the substrate is separated by the breaking process.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Figure 1:
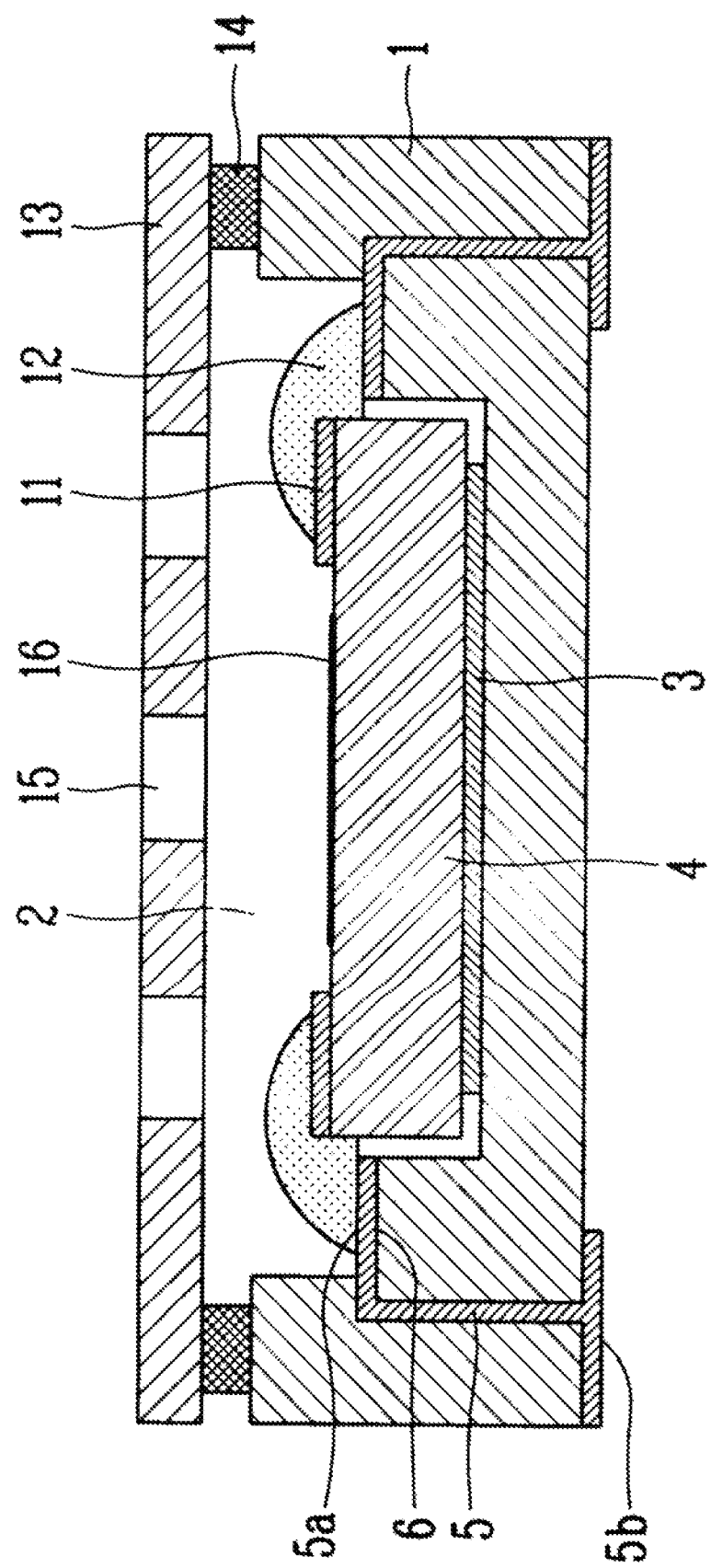
FIG. 1 is a longitudinal sectional view showing a conventional micro package for a gas sensor.
Figure 2:
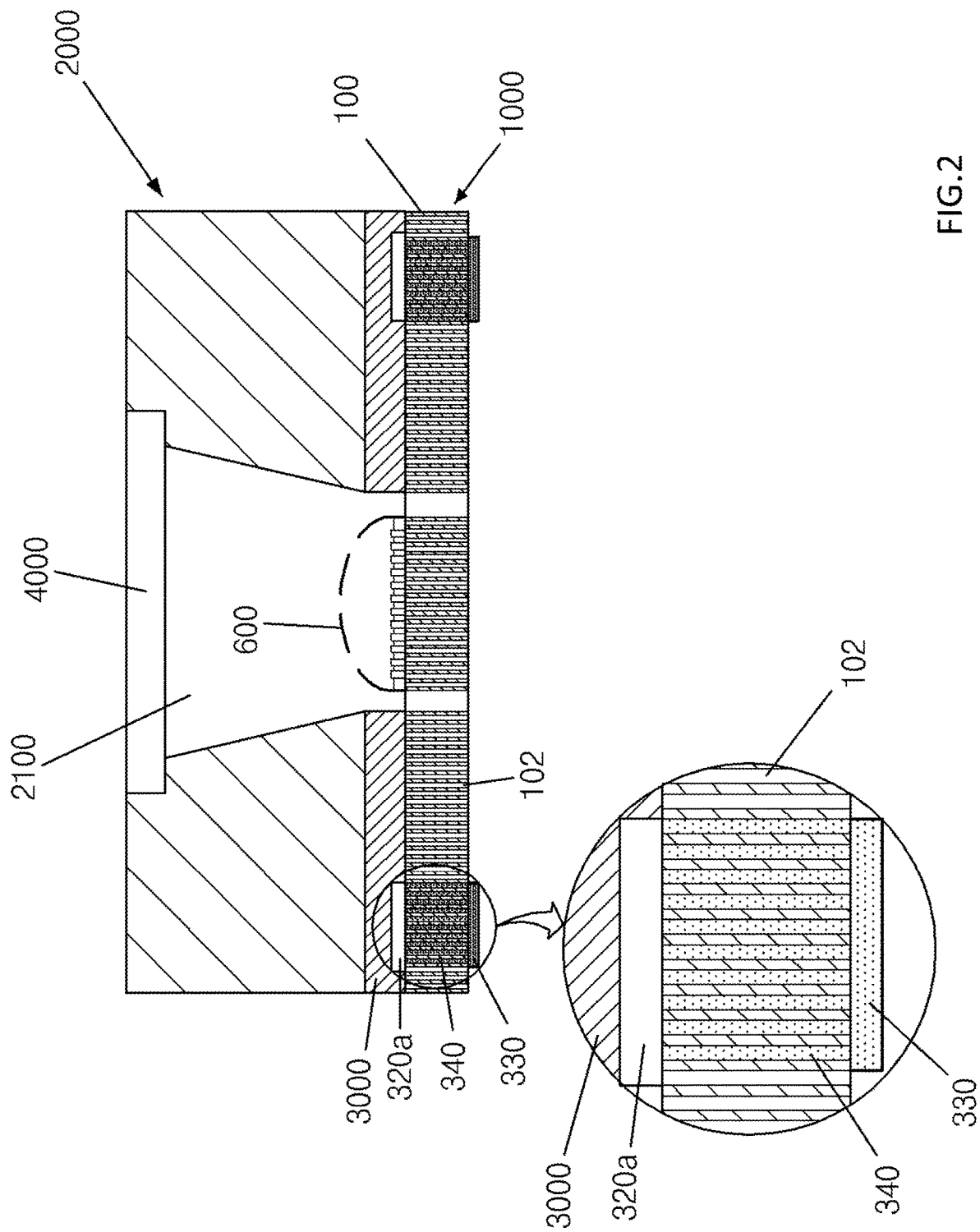
FIG. 2 is a sectional view showing a microsensor package according to an exemplary embodiment of the present invention.

Hereinbelow, exemplary embodiments of the present invention will be described in detail with reference to the accompanying drawings.

For reference, in the following description, the same configurations of the present invention as those of the related art will not be described in detail. Reference is made to the foregoing description of the related art.

When it is said that any part is positioned "on" another part, it means the part is directly on the other part or above the other part with at least one intermediate part. In contrast, if any part is said to be positioned "directly on" another part, it means that there is no intermediate part between the two parts.

Technical terms used here are to only describe a specific exemplary embodiment and are not intended to limit the present invention. Singular forms used here include a plurality of forms unless phrases explicitly represent an opposite meaning. A meaning of "comprising" used in a specification embodies a specific characteristic, area, integer, step, operation, element and/or component and does not exclude presence or addition of another specific characteristic, area, integer, step, operation, element, component and/or group.

Terms such as "lower" and "upper" representing relative space may be used for more easily describing a relationship to another portion of a portion shown in the drawings. Such terms are intended to include other meanings or operations of a using apparatus together with a meaning that is intended in the drawings. For example, when an apparatus is inverted in the drawings, any portion described as disposed at a "lower" portion of other portions is described as being disposed at an "upper" portion of other portions. Therefore, an illustrative term of "lower" includes entire upper and lower directions. An apparatus may rotate by 90° or another angle, and a term representing relative space is accordingly analyzed.

As shown in FIGS. 2 to 6, a microsensor package according to the embodiment includes a sensing chip 1000, wherein the sensing chip 1000 includes a substrate 100, and a sensor electrode 300 provided on the substrate 100; the sensor electrode 300 includes a sensor wire, and a sensor electrode pad connected to the sensor wire; the substrate 100 is provided with a plurality of pores 102 formed in vertical directions; the substrate 100 is provided with a bonding portion 330 on a lower surface thereof; the pores 102 under the sensor electrode pad are formed through the substrate in the vertical directions; and the pores 102 under the sensor electrode pad are provided therein with respective connecting portions 340 electrically connecting the sensor electrode pad and the bonding portion 330 to each other.

The sensing chip 1000 includes the substrate 100, and the sensor electrode 300 formed on the substrate 100.

When anodizing a metallic base material, an anodized film is formed. The anodized film is composed of a porous layer having a plurality of pores on the surface (upper surface) and a barrier layer existing at the lower portion of the porous layer. Here, the metallic base material may be aluminum (Al), titanium (Ti), tungsten (W), zinc (Zn), etc. It is preferred that the metallic base material be made of aluminum or aluminum alloy material that is lightweight, is easy to process, is excellent in thermal conductivity, and obviates concern about heavy metal contamination.

For example, when anodizing the surface of aluminum, an alumina film is formed. The alumina film is composed of a porous alumina layer having a plurality of pores 102 penetrating the surface (upper surface) in vertical directions and a barrier layer existing at the lower portion of the porous alumina layer. According to the embodiment of the present invention, the substrate 100 may be composed of only the porous alumina layer through which the pores 102 penetrate in vertical directions by removing the barrier layer of the alumina film. Alternatively, the substrate may be configured such that some of the barrier layer is removed to the pores formed with a sensor electrode pad to vertically penetrate.

By removing the aluminum and the barrier layer from the anodized aluminum (AAO), the pores 102 of the substrate 100 vertically penetrate. The substrate 100 is composed of the porous alumina layer, whereby insulation performance is improved.

The diameter of the pore 102 is formed in nanometers.

The substrate 100 may be provided in the form of a quadrangular plate when viewed in a plan view.

The substrate 100 includes: a first supporting portion 110 formed at a center of the substrate 100; a second supporting unit 120 formed outside of the first supporting portion 110 being spaced apart from the first supporting portion 110; and a bridge portion connecting the first supporting portion 110 and the second supporting unit 120. The first supporting portion 110 is provided in a cylindrical shape overall, with a plurality of bridge portions connected to the outer circumference thereof.

Further, in the substrate 100, a plurality of air gaps 101 is formed near the first supporting portion 110, namely, between the first supporting portion 110 and the second supporting unit 120.

The air gaps 101 are formed by penetrating vertically the substrate. In other words, the air gaps 101 are spaces formed by penetrating from an upper surface of the substrate 100 to a lower surface thereof.

The maximum width (lateral width) of the air gap 101 is wider than that of the pore 102, and than that of the sensor wire or a heating wire 210. The air gap 101 is formed in an arc shape, and four air gaps are formed. A plurality of air gaps 101 are arranged circumferentially spaced apart from each other.

A plurality of air gaps may be discontinuously formed. The air gaps 101 and the bridge portions are alternately placed around the first supporting portion 110.

Accordingly, the first supporting portion 110 and the second supporting portion 120 are spaced apart from each other by the air gap 101 at a portion other than the bridge portion. The bridge portions are formed by discontinuously forming the air gaps 101 through etching the periphery of the first supporting portion 110. Thus, a first end of each bridge portion is connected to the first supporting portion 110, and a second end thereof is connected to the second supporting portion 120. The first supporting portion 110 and the second supporting portion 120 are connected to each other at four locations by four bridge portions.

The sensor electrode 300 is formed on the upper surface of the substrate 100.

The sensor electrode 300 detects the changes in the electrical characteristics when the gas is adsorbed onto the sensing material 600.

The sensor electrode 300 includes a first sensor electrode 300a and a second sensor electrode 300b spaced apart from the first sensor electrode 300a. The first sensor electrode 300a and the second sensor electrode 300b are spaced apart from each other, and are symmetrical based on the vertical center line on the plane.

Each of the first and second sensor electrodes 300a and 300b includes the sensor wire formed on the first supporting portion 110, and a sensor electrode pad formed on both the bridge portion and the second supporting portion 120 by being connected to the sensor wire.

The first sensor electrode 300a includes a first sensor wire 310a formed on the upper surface of the first supporting portion 110, and a first sensor electrode pad 320a connected to the first sensor wire 310a.

The second sensor electrode 300b includes a second sensor wire 310b formed on the upper surface of the first supporting portion 110, and a second sensor electrode pad 320b connected to the second sensor wire 310b.

The sensor wire includes the first sensor wire 310a and the second sensor wire 310b. The sensor electrode pad includes the first sensor electrode pad 320a and the second sensor electrode pad 320b. The width of the sensor wire is fixed. The sensor electrode pad is placed on the upper surface of the bridge portion and the second supporting portion 120, and has a width wider than the widths of the first sensor wire 310a and the second sensor wire 310b. The widths of the sensor electrode pads of the first and the second sensor electrodes 300a and 300b are wider towards the end portions. That is, the widths of the sensor electrode pads are gradually reduced towards the first sensor wire 310a and the second sensor wire 310b.

The sensor electrode 300 is formed of a mixture including at least one of Pt, W, Co, Ni, Au, and Cu.

A heater electrode 200 is formed on the upper surface of the substrate 100.

The pores 102 placed at the lower portion of the heater electrode 200 and the sensor electrode 300 has the blocked upper portion and the opened lower portion.

The heater electrode 200 includes: a heating wire 210 closer to a sensor wire than to a sensor electrode pad by being formed on the first supporting portion 110; and heater electrode pad formed on the second supporting portion 120 and the bridge portion by being connected to the heating wire 210.

The heating wire 210 is formed on the first supporting portion 110, and surrounds at least a part of the first sensor wire 310a and the second sensor wire 310b. The heater electrode pad includes a first heater electrode pad 220a and a second heater electrode pad 220b spaced apart from each other by respectively being connected to both ends of the heating wire 210.

When viewed in a plan view, the heating wire 210 is formed to be symmetrical about the vertical center line of the first supporting portion 110, and includes a plurality of arc portions formed in arc shapes and several connecting portions connecting the arc portions.

Figure 3:
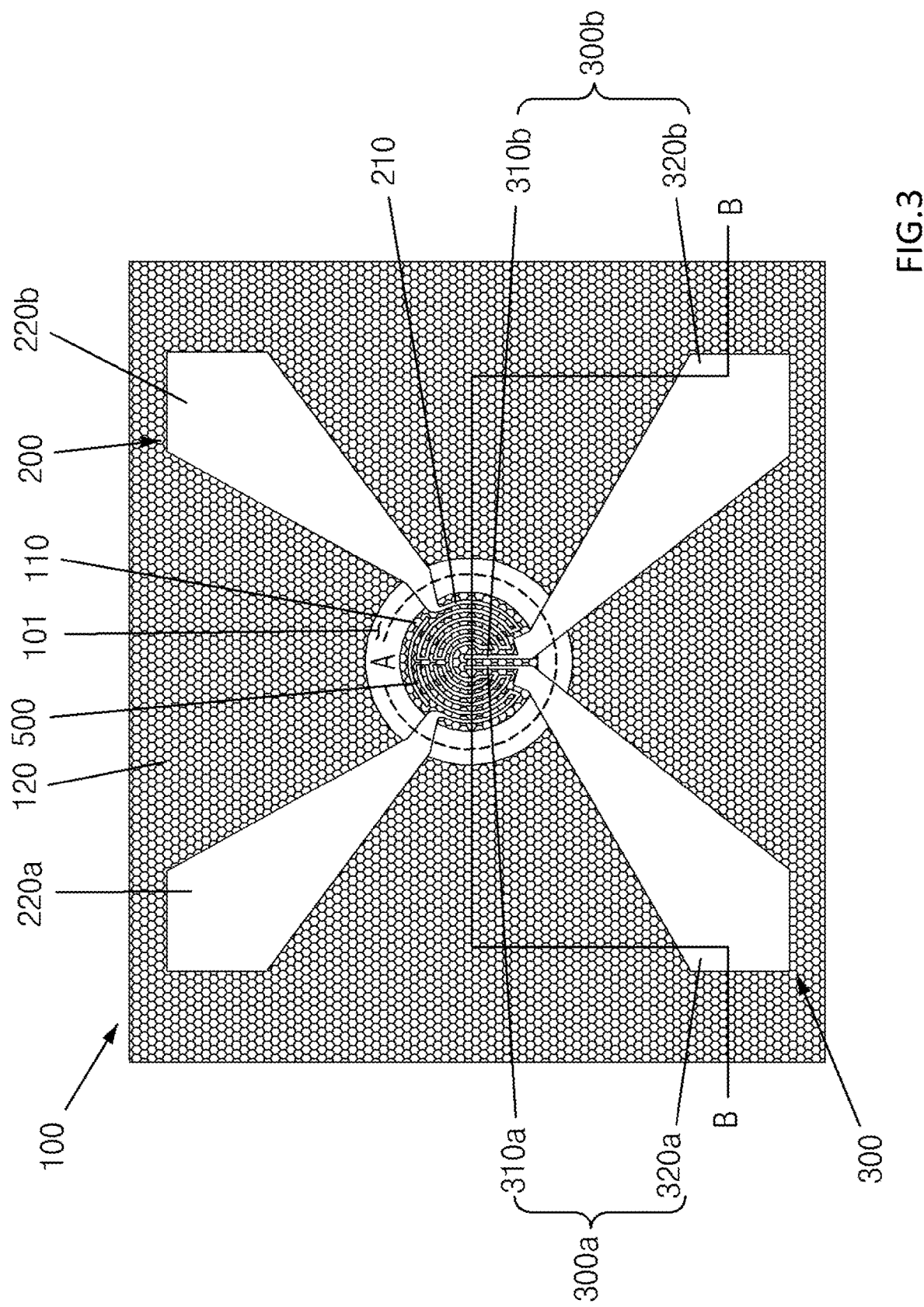
FIG. 3 is a plan view showing a sensing chip of the microsensor package of FIG. 2.
Figure 4:
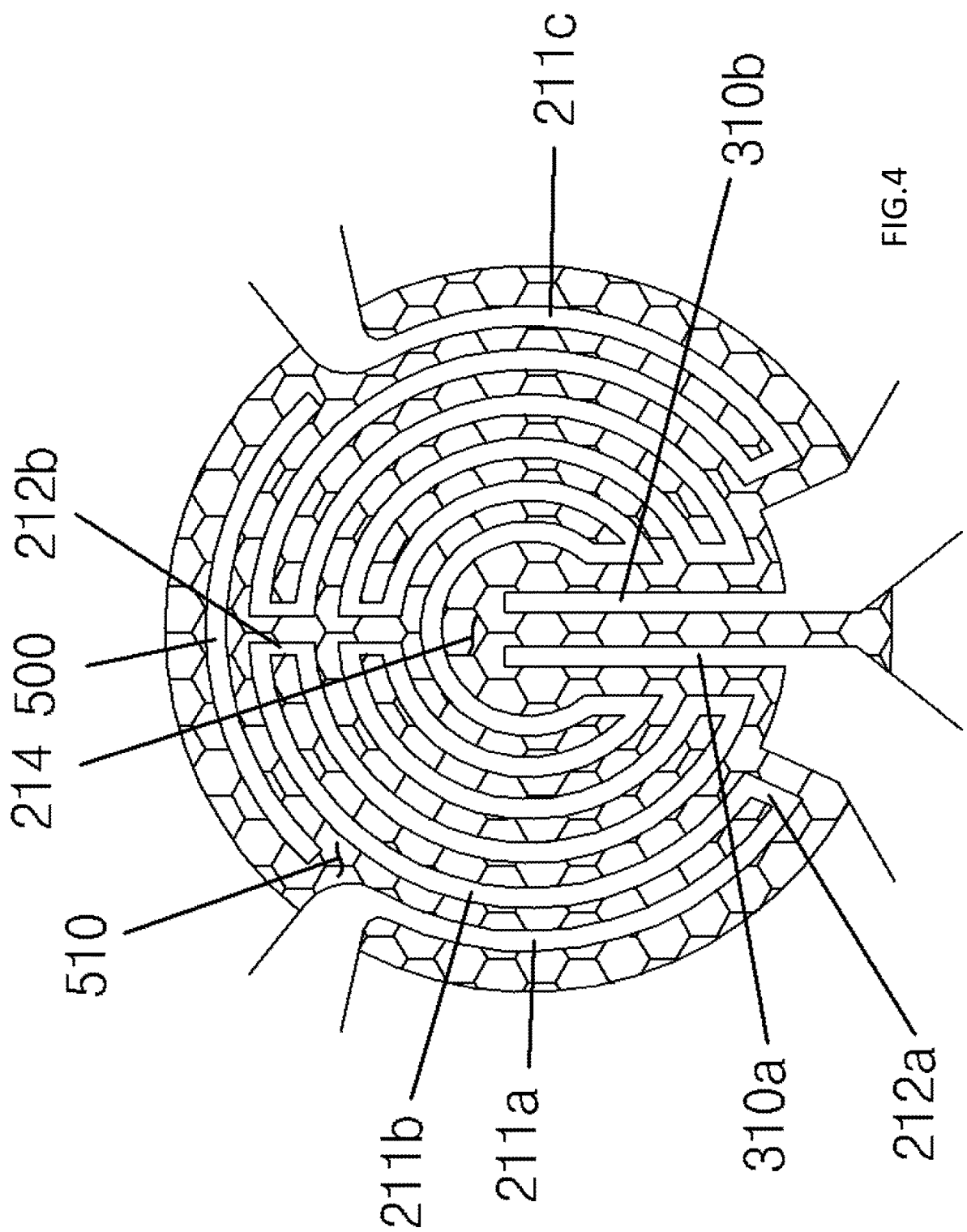
FIG. 4 is an enlarged view of A portion of FIG. 3.

As shown in FIG. 3, the heating wire 210 includes: a first arc portion 211a formed in an arc shape close to the air gap 101; a first connecting portion 212a extending from an end of the first arc portion 211a and bent toward the inside of the first supporting portion 110; a second arc portion 211b in an arc shape extending from an end of the first connecting portion 212a and spaced apart from the first arc portion 211a inwards; a second connecting portion 212b extending from an end of the second arc portion 211b toward the inside of the first supporting portion 110; and a third arc portion 211c. In this manner, several arc portions and connecting portions are formed by being repeatedly connected to each other.

The heating wire 210 is connected from the first arc portion 211a to the third arc portion 211c to have an integral body.

A plurality of arc portions of the heating wire 210 are formed in a half-arc shape. Thus, the heating wire 1210 is overall in a circular shape. Accordingly, temperature uniformity of the first supporting portion 110 and the sensing material 600 may be enhanced.

The central portion of the heating wire 210 is a point where opposite arc portions meet, and the central point is in a left side opened circular shape by joining two arc portions together. An isolated space portion 214 is formed inside of the central portion. The isolated space portion 214 is formed by extending from central portions of the first supporting portion 110 and the heating wire 210 to the outermost of the first supporting portion 110 and the heating wire 210. The sensor wire is placed at the isolated space portion 214. Further, a second end portion of the first arc portion 211a is connected to the first heater electrode pad 220a, and a first end portion of the third arc portion 211c is connected to the second heater electrode pad 220b.

The heater electrode 200 is formed of a mixture including at least one of Pt, W, Co, Ni, Au, and Cu.

In the meantime, a dummy metal 500 is formed between both ends of the heating wire 210, namely, the ends of the first arc portion 211a and the third arc portion 211c respectively connected to the first heater electrode pad 220a and the second heater electrode pad 220b. The dummy metal 500 is formed on the upper surface of the first supporting portion 110.

The dummy metal 500 is formed in an arc shape between the air gap 101 and the heating wire 210 of the heater electrode 200. The dummy metal 500 is spaced apart from the heating wire 210 adjacent thereto.

It is desired that the dummy metal 500 is formed outside of the heating wire 210 and is a metal. The material of the dummy metal 500 may be the same as the electrode material, and the electrode material may be a metal such as platinum, aluminum, copper, etc.

The central angles of the first arc portion 211a and the third arc portion 211c are small, compared to the remaining arc portions placed inside thereof. At the outer circumference of the heating wire 210, a space 510 is defined between the ends of the first arc portion 211a and the third arc portion 211c. The dummy metal 500 is placed at the space 510.

The space 510 at the outer circumference of the heating wire 210 is partially filled by the area of the dummy metal 500. Thus, when viewed in a plan view, the outer circumference of the heating wire 210 and the dummy metal 500 is in a circular shape, whereby temperature uniformity of the first supporting portion 110 may be enhanced. Accordingly, temperature distribution of the heating wire 210, which is heated by low power, on the first supporting portion 110 is more uniform.

The heater electrode pad includes the first and the second heater electrode pads 220a and 220b that are respectively connected to both ends of the heating wire 210. As described above, at least two heater electrode pads are formed. The widths of the heater electrode pads are wider towards the outside. In other words, the widths of the heater electrode pads are narrower towards the heating wire 210. The width of the heater electrode pad is wider than the width of the heating wire 210.

The heater electrode pad and the sensor electrode pad are placed in radial directions with respect to the first supporting portion 110. The end portions of both the heater electrode pad and the sensor electrode pad are arranged close to each corner of the substrate 100 and are spaced apart from each other.

An anti-discoloration protective layer (not shown) is formed on a part of an upper portion of the heater electrode 200 and the sensor electrode 300. The anti-discoloration protective layer may be formed of an oxide type material. Moreover, the anti-discoloration protective layer may be formed of at least one of tantalum oxide (TaOx), titanium oxide ($TiO_2$), silicon oxide ($SiO_2$), and aluminum oxide ($Al_2O_3$).

The heating wire 210 and the first and the second sensor wires 310a and 310b are surrounded by the air gap 101. In other words, the air gap 101 is placed around the heating wire 210 and the first and the second sensor wires 310a and 310b. The air gap 101 is placed at the sides of the heating wire 210 and the first and the second sensor wires 310a and 310b.

Specifically, the air gaps 101 are placed between the first heater electrode pad 220a and the first sensor electrode pad 320a of the first sensor electrode 300a, between the first heater electrode pad 220a and the second heater electrode pad 220b, between the second heater electrode pad 220b and the second sensor electrode pad 320b of the second sensor electrode 300b, and between the second sensor electrode pad 320b of the second sensor electrode 300b and the first sensor electrode pad 320a of the first sensor electrode 300a. In other words, the air gaps 101 are formed at an area except for the portion supporting the heater electrode 200 and the sensor electrode 300.

Due to the air gap 101, on the substrate 100, formed are the first supporting portion 110 supporting the heating wire 210 and the sensor wire in common; and the second supporting portion 120 and the bridge portion that supports the heater electrode pad and the sensor electrode pad.

The area of the first supporting portion 110 is wider than the area of the heating wire 210 and the sensor wire.

On the first supporting portion 110, a sensing material 600 is formed to cover the heating wire 210 and the sensor wire. That is, the sensing material 600 is formed at a position corresponding to the first supporting portion 110. The sensing material 600 is formed by being printed. When the sensing material 600 is printed, the print in a mesh-net shape remains on the surface of the sensing material 600 after forming the sensing material 600.

The substrate 100 is formed with a bonding portion 330 on the lower surface thereof. In other words, at the substrate 100, the bonding portion 330 is formed on a surface opposite to a surface on which the sensor electrode pad or the heater electrode pad is formed. Further, the bonding portion 330 is disposed at a location corresponding to a location of the sensor electrode pad or the heater electrode pad.

The bonding portion 330 is mounted on a printed circuit board (PCB).

The pores 102 under the sensor electrode pad or under the heater electrode pad is formed to vertically penetrate. The pores 102 disposed between the sensor electrode pad or the heater electrode pad and the bonding portion 330 is formed to vertically penetrate.

In other words, the pores 102 are formed to penetrate from the surface on which the sensor electrode pad or the heater electrode pad is formed, to a surface opposite thereto.

A plurality of pores 102 under the sensor electrode pad or under the heater electrode pad is provided therein with connecting portions 340 electrically connecting the sensor electrode pad or the heater electrode pad with the bonding portion 330. The connecting portion 340 is formed in a columnar shape having a diameter of nanometers.

When the bonding portion 330 is electrically connected to the printed circuit board (PCB), it is possible to supply power to the heater electrode 200, and possible to sense the signal of the sensor electrode 300.

As described above, the bonding portion 330 to be mounted on the printed circuit board (PCB) is formed on the lower surface of the substrate 100, and the connecting portions 340 are formed in the pores 102 to connect the sensor electrode pad or the heater electrode pad formed on the upper surface of the substrate 100, with the bonding portion 330, whereby the connecting portions 340 can be formed without any separate etching operation and can be mounted to the printed circuit board in the form of a SMD (surface mount device) without wire bonding, thereby facilitating the mounting of the microsensor package. Further, it is possible to make the microsensor package light, slim, and compact.

A sensor cap 2000 is provided at an upper portion of the sensing chip 1000 to cover the sensing chip 1000. The lower surface of the sensor cap 2000 is bonded to the upper portion of the sensing chip 1000 through a bonding agent.

The sensor cap 2000 is provided in the form of a quadrangular plate.

The sensor cap 2000 is made of a plastic or a polymer material, whereby it has no effect on the reaction gas, and has high durability and excellent manufacturability.

Further, the sensor cap 2000 is made of a material with a shrinkage coefficient or an expansion coefficient equal to or similar to that of the substrate 100, whereby the manufacture thereof is further facilitated, and it is possible to prevent the sensor cap 2000 and the substrate 100 from being separated even if they contract or expand.

For example, as described above, the substrate 100 is made of an anodized aluminum oxide (AAO) material, and the sensor cap 2000 is made of a ceramic material, whereby it is possible to prevent the heat of the heater electrode 200 formed on the sensing chip 1000 from being transmitted to a portion other than the sensing material 600, at the same time, mass production is facilitated, and it is possible to prevent the sensor cap 2000 and the substrate 100 from being separated even if they contract or expand.

The sensor cap 2000 is formed with a cavity 2100 penetrating vertically. The cavity 2100 is tapered so that the horizontal cross-sectional area of the cavity 2100 is gradually reduced as it goes downward, that is, toward the sensing chip 1000. Accordingly, gas is supplied smoothly to the sensing chip 1000.

The sensor wire, the heating wire 210, the first supporting portion 110, the air gaps 101, and the sensing material 600 are disposed inside the cavity 2100, so that the gas can be effectively delivered to the gas sensing portion of the sensing chip 1000.

In other words, the inner wall of the sensor cap 2000 surrounds the first supporting portion 110.

The microsensor package further includes an AAO filter 4000 covering an upper portion of the cavity 2100, and gas is supplied to the sensing chip 1000 after passing through the AAO filter 4000.

A filter seating groove on which the AAO filter 4000 is seated may be formed in the upper portion of the sensor cap 2000 to communicate with the cavity 2100. Due to the filter seating groove, the mounting of the AAO filter 4000 is further facilitated.

The AAO filter 4000 is bonded to the upper portion of the sensor cap 2000 through a bonding agent. The AAO filter 4000 has a plurality of nano-sized pores penetrating vertically. The pores of the AAO filter 4000 communicate with the cavity 2100. Accordingly, it is possible to effectively prevent foreign matter from being introduced into the gas sensing portion.

Further, the inside of the pores of the AAO filter 4000 is coated with a hydrophobic material, whereby it is possible to prevent moisture penetration into the gas sensing portion.

Hereinafter, the operation of the embodiment having the above-described configuration will be described.

In order to measure the gas concentration, first, the same electric power is applied to two heater electrode pads 220 of the heater electrode 200 so as to heat the sensing material 600 to a predetermined temperature.

The gas inside the cavity 2100 through the AAO filter 4000 is adsorbed onto or desorbed from the heated sensing material 600.

Accordingly, electrical conductivity between the first sensor wire 310a and the second sensor wire 310b changes, thereby detecting gas.

Further, for more precise measurement, a target gas concentration is measured after resetting the sensing material 600 to its initial state through high temperature heating, thereby forcibly removing gas species or moisture being already adsorbed onto the sensing material 600.

Figure 5:
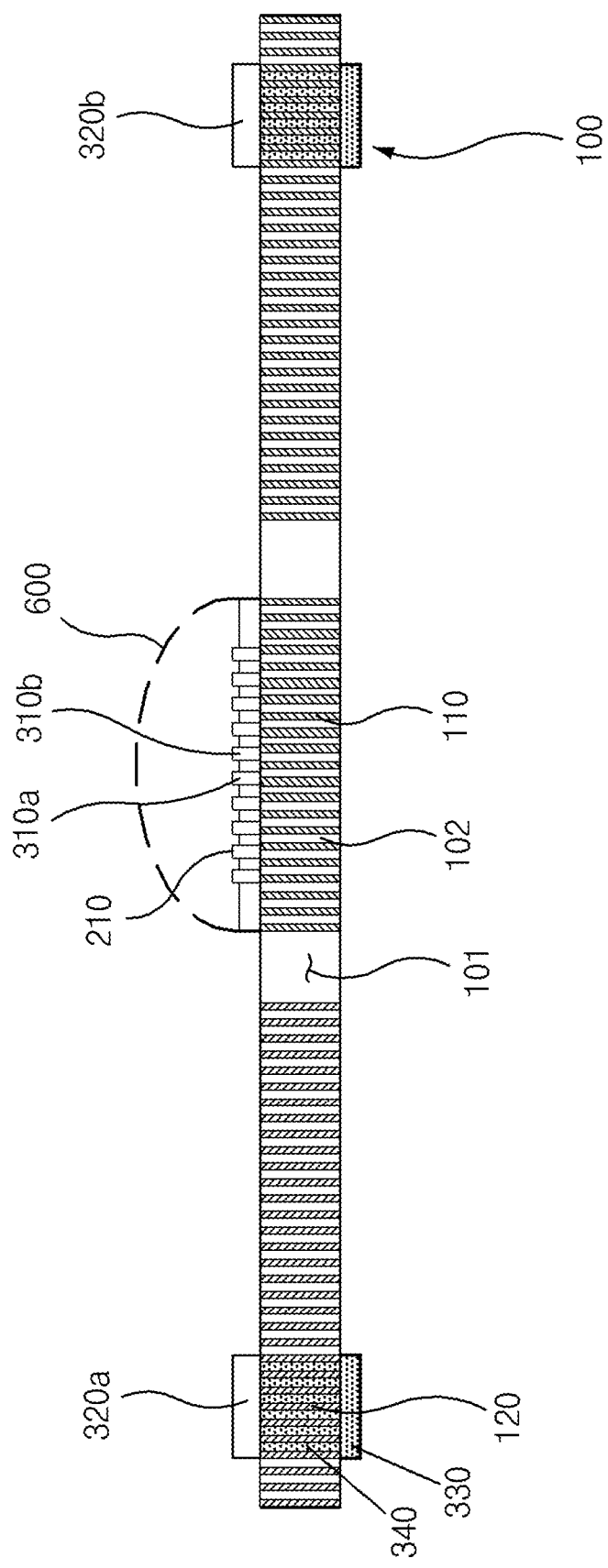
FIG. 5 is an enlarged view taken along line B-B of FIG. 3.
Figure 6:
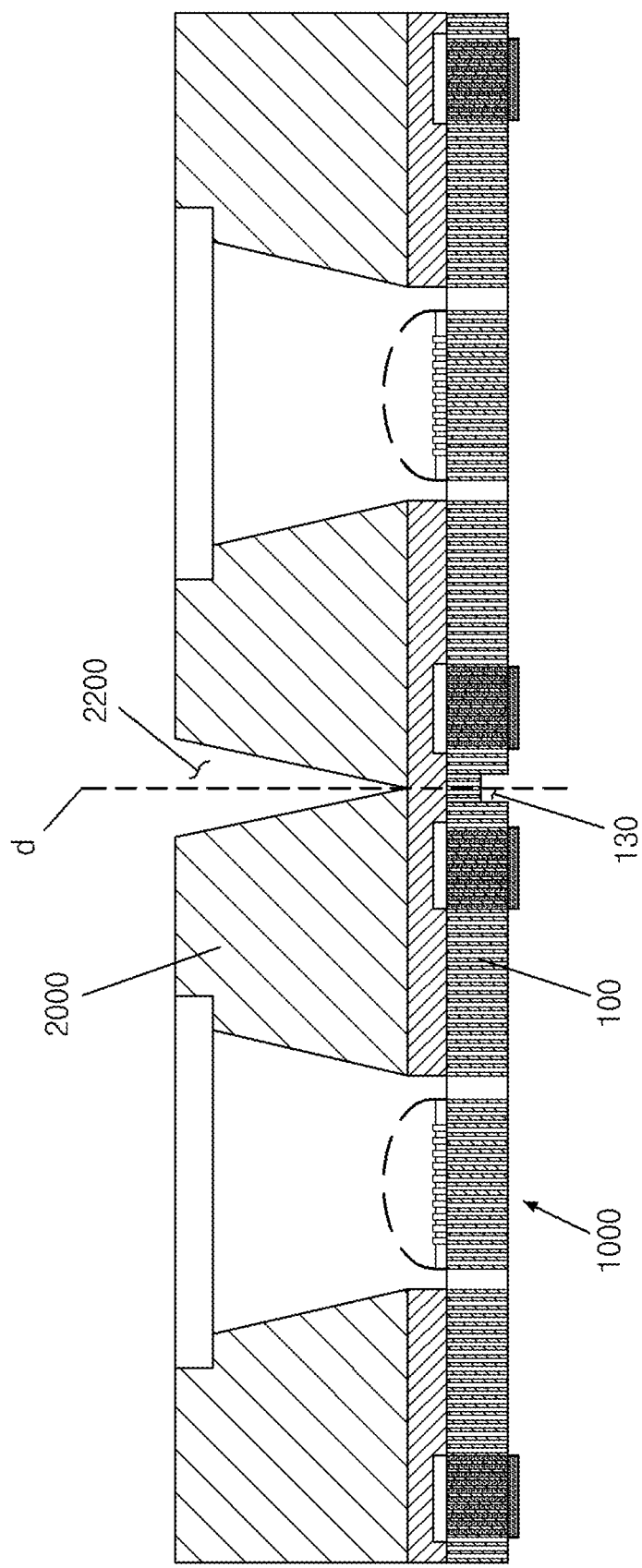
FIG. 6 is a sectional view showing a state where a plurality of microsensor packages according to an exemplary embodiment of the present invention is manufactured simultaneously.

Meanwhile, as shown in FIG. 5, in order to produce a plurality of microsensor packages simultaneously, a plurality of sensor electrodes 300 and heater electrodes 200 may be formed on one substrate 100.

The substrate 100 is provided on the upper or lower surface thereof with a first cut groove 130 disposed between two neighboring the sensor electrodes 300. In the embodiment, the first cut groove 130 is formed on the lower surface of the substrate 100, which is a surface opposite to a surface on which the sensor cap 2000 is provided.

Further, the sensor cap 2000 is provided on an upper surface thereof with a second cut groove 2200 disposed between two neighboring the sensor electrodes 300. In other words, in the sensor cap 2000, the second cut groove 2200 is vertically formed on a surface opposite to a surface facing the substrate 100.

The second cut groove 2200 is tapered so that the width thereof is gradually reduced toward the sensing chip 1000.

Since the unit package can be separated by a simple breaking process through the first and second cut grooves 130 and 2200, the manufacturing process is simplified since there is no need to cut using a blade.

Further, since the sensor cap 2000 has a vertical thickness greater than that of the substrate 100, the substrate 100 of the sensing chip 1000 can be cut smoothly when the sensor cap 2000 with the substrate 100 is separated by the breaking process.

As described above, although the exemplary embodiments of the present invention have been disclosed, those skilled in the art will appreciate that various modifications or changes are possible, without departing from the scope and spirit of the invention as disclosed in the accompanying claims.

What is claimed is:

1. A microsensor package comprising:
   a sensing chip,
   wherein the sensing chip includes:
      a substrate;
      a sensor electrode provided on the substrate, the sensor electrode including a sensor wire and a sensor electrode pad connected to the sensor wire; and
      a sensing material formed to cover the sensor wire,
   wherein a bonding portion is provided on a lower surface of the substrate, so as to be electrically connected to a printed circuit board (PCB),
   wherein the substrate is made of an anodized aluminum oxide (AAO) material, and the substrate is provided with a first plurality of pores formed by removing an aluminum and a barrier layer from the AAO material in a vertical direction,
   wherein a second plurality of pores under the sensor electrode pad among the first plurality of pores are formed through the substrate in the vertical direction,
   wherein each of the second plurality of pores under the sensor electrode pad is provided therein with a respective one of connecting portions electrically connecting the sensor electrode pad and the bonding portion to each other, and
   wherein each of the connecting portions electrically connecting the sensor electrode pad and the bonding portion is formed in a columnar shape.

2. The microsensor package of claim 1, wherein the sensing chip is provided with a sensor cap at an upper portion thereof,
   the sensor cap has a cavity formed therethrough in the vertical direction, and
   the sensor wire is disposed in a lower portion of the cavity.

3. The microsensor package of claim 2, further comprising:
   an anodized aluminum oxide (AAO) filter covering an upper portion of the cavity.

4. The microsensor package of claim 3, wherein the AAO filter is coated with a hydrophobic material.

5. The microsensor package of claim 2, wherein the sensor cap is made of a material selected from the group consisting of ceramics, plastics, polymers, and aluminum oxides.

6. The microsensor package of claim 2, wherein the sensor cap is made of a material with a shrinkage coefficient or an expansion coefficient equal or similar to a shrinkage coefficient or an expansion coefficient of the substrate.

7. The microsensor package of claim 2,
   wherein the sensor cap is made of a ceramic material.

8. The microsensor package of claim 2, wherein the sensor electrode is a first sensor electrode, further comprising a second sensor electrode provided the substrate and neighboring the first sensor electrode, and
   an upper surface of the sensor cap is provided with a second cut groove disposed between the first and second sensor electrodes.

9. The microsensor package of claim 8, wherein the second cut groove has a width gradually reduced in a down direction.

10. The microsensor package of claim 8, wherein the sensor cap has a vertical thickness greater than a vertical thickness of the substrate.

11. The microsensor package of claim 1, wherein the sensor electrode is a first sensor electrode, further comprising a second sensor electrode provided on the substrate and neighboring the first sensor electrode, and
    an upper or the lower surface of the substrate is provided with a first cut groove disposed between the first and second sensor electrodes.

* * * * *